US00PP11062P

United States Patent [19]

Winchel

[11] Patent Number: Plant 11,062

[45] Date of Patent: Sep. 14, 1999

[54] HYBRID TEA ROSE PLANT NAMED 'BURWINDISARY'

[75] Inventor: Joseph F Winchel, Long Beach, Calif.

[73] Assignee: Meredith Corporation, Des Moines, Iowa

[21] Appl. No.: 08/962,598

[22] Filed: Oct. 31, 1997

[51] Int. Cl.[6] ..... A01H 5/00

[52] U.S. Cl. ..... Plt./132

[58] Field of Search ..... Plt./11, 12, 22, Plt./130, 131, 132, 140, 142, 143

*Primary Examiner*—Howard J. Locker

*Attorney, Agent, or Firm*—Banner & Witcoff, Ltd.

[57] ABSTRACT

A new and distinct variety of a hybrid tea rose plant named Burwindisary which is characterized by its upright growth habit with flowers borne singly on stems having an ivory cast on lower petals with a raspberry color on petal edges.

1 Drawing Sheet

The present invention relates to a new and distinctive variety of rose plant of the Hybrid Tea class, originating by my crossing of an Unnamed Hybrid Tea as a seed parent which was located in proximity to Hybrid Tea Roses, with an unknown Hybrid Tea class rose as the pollen parent.

The new variety Hybrid Tea rose plant possesses many exceptional characteristics including:

(a) Upright growth habit; branching in upper growth with flowers borne on single stems;

(b) ivory cast on lower petals with raspberry color on petal edges.

The new varieties can be grown to produce attractive cut flowers in greenhouses or outdoors to fulfill the needs of the floriculture industry.

The plant has been reproduced outdoors in Kern County, Calif. where asexual reproduction has taken place by budding onto an understock of Dr. Huey. The asexual reproduction shows that the aforementioned and all other distinctive characteristics are transmited from one generation to another.

The new variety has been named the 'Burwindisary' variety.

The accompanying photographic illustration shows the foliage and the bloom of the new plant in varying stages of maturity, with the colors depicted being as nearly true as is reasonably possible to attain in photographic reproductions of this type.

The following is a detailed description of my new variety, with color terminology in accordance with The Royal Horticulture Society Colour Chart (R.H.S.C.C.). The terminology used in the color description herein refers to plate numbers in the aforementioned color chart, e.g., "155B" is plant "155B" of The Royal Horticulture Society Colour Chart.

Parentage:

*Seed parent.*—Unnamed, but located in proximity to other hybrid tea roses.

*Pollen parent.*—Unknown.

Class: Hybrid Tea.

The following observations are made of specimens grown outdoors in Tyler, Tex. year round.

FLOWER

Blooming habit

A. Bud:
- (1) *Size.*—Fully mature, sepals enclosed, about 2 to 2⅛ in. from base of petals.
- (2) *Form.*—Urn.
- (3) *Sepals.*—1½ in. in length.
- (4) *Peduncle.*—Length about ¾ inch, erect, color near 144B.
- (5) *Bracts.*—None present.
- (6) *Color.*—155B at base, near 66A at top.

B. Bloom.
- (1) *Size.*—Average size around 3 in. when open.
- (2) *Shape.*—Usually does not flatten with age.
- (3) *Borne.*—Usually singly or in small clusters of blooms.
- (4) *Form.*—Usually high centers.
- (5) *Petalage.*—Usually around 40 petals.
- (6) *Color.*—Outer petals: Top surface: near 57A. Underside: near 58C. Edge: near 67C. Inner petals: Top surface at base: near 155C. Underside at base: near 155C. Edge: near 158D. Base of Petal Color: near 157A. General tonality from a distance: 157B. Color fully open: Outer petals: Top surface at base: 157C. Underside: Same. Edge: 57B. Inner petals: Top surface at base: 157C. Undersurface: same. Edge: 57B. Base of petals: Color 157C. Color change: Blooms get lighter upon finish. Top surface: 157C to 57B. Undersurface: 157C to 58B. General tonality at a distance: 157C.

C. Petals:
- (1) *Texture.*—Satiny.
- (2) *Appearance.*—Elliptical.
- (3) *Form.*—Imbricated.
- (4) *Arrangement.*—Layered, evenly distributed.
- (5) *Petaloids.*≦Few in number; color near 19C.
- (6) *Persistence.*—Average, about 5 days after being fully open.
- (7) *Fragrance.*—Slightly Spicy.
- (8) *Lasting quality.*—About 7 days on the plant, about 4 days as a cut flower.

REPRODUCTIVE ORGANS

A. Stamen:
- (1) *Arrangement.*—Regularly arranged around styles.
- (2) *Length.*—Uneven.
- (3) *Color.*—158A.

(4) *Filaments.*—Color — 157C.
(5) *Annthers.*—Color — 157D.
(6) *Pollen.*—Color — 10C.

B. Pistil:
(1) *Stigma.*—Color 41B.
(2) *Ovary.*—Shape — orbicular; average diameter 0.5 in.; average height 0.75 in.

Hips:
(1) *Shape.*—Globular.
(2) *Size.*—Average one in.
(3) *Color.*—31B.
(4) *Seeds.*—None protruding.

PLANT

A. Form: Upright with uniform branching.
B. Growth: Moderate.
*Height.*—4' at maturity.
C. Stem: Length about 8 inches under average conditions.
D. Foliage: Compound of 5 leaflets, medium size, abundant quantity
(1) *Mature size.*—3 leaflet leaf 1.5 to 2.5 in., measured from base of stipule to terminal leaflet tip.
(2) *Color.*—New foliage upper side 183C; underside 148C. Mature foliage upper side 147A; underside 147C.
(3) *Shape.*—Elliptic.
(4) *Texture.*—Smooth.
(5) *Petiole.*—Color 158C.
(6) *Stipule.*—Color near 161B.
(7) *Edge.*—Serrated with regular symmetry.

Wood:
*New wood.*—Color 148B with smooth bark.
*Old wood.*—Color 147B with rough bark.

F. Thorns:
*Color.*—165A. Ordinarily thin with slight down curve and medium length; spaced at about 12 nodes.

G. Prickles: Color near 185B.

I claim:

1. A new and distinct variety of the rose plant of the Hybrid Tea class, substantially as herein shown and described.

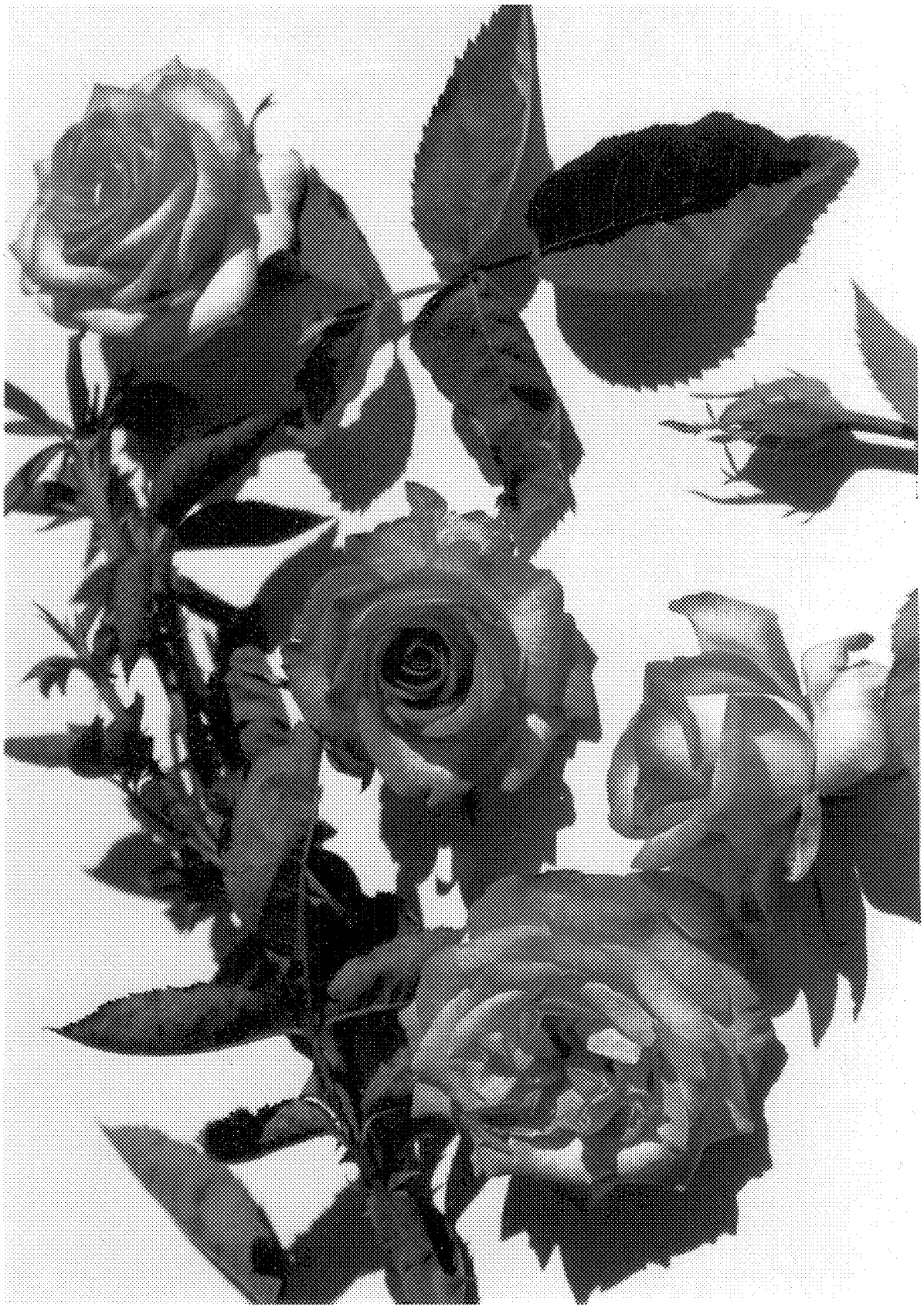

* * * * *